(12) United States Patent
Armitage et al.

(10) Patent No.: US 11,359,151 B2
(45) Date of Patent: Jun. 14, 2022

(54) METHODS FOR PREPARING FUEL ADDITIVES

(71) Applicant: BP OIL INTERNATIONAL LIMITED, Middlesex (GB)

(72) Inventors: Gareth Gerald Armitage, Hull (GB); Jon Michael Stewart Deeley, Hull (GB); Sorin Vasile Filip, Reading (GB); John Glenn Sunley, Hull (GB)

(73) Assignee: BP OIL INTERNATIONAL LIMITED, Sunbury on Thames (GB)

( * ) Notice: Subject to any disclaimer, the term of this patent is extended or adjusted under 35 U.S.C. 154(b) by 4 days.

(21) Appl. No.: 16/958,734

(22) PCT Filed: Dec. 19, 2018

(86) PCT No.: PCT/EP2018/086024
§ 371 (c)(1),
(2) Date: Jun. 28, 2020

(87) PCT Pub. No.: WO2019/129590
PCT Pub. Date: Jul. 4, 2019

(65) Prior Publication Data
US 2020/0332211 A1    Oct. 22, 2020

(30) Foreign Application Priority Data

Dec. 27, 2017 (GB) .................................... 1721961

(51) Int. Cl.
*C10L 1/233* (2006.01)
*C07D 265/36* (2006.01)
*C10L 10/10* (2006.01)

(52) U.S. Cl.
CPC ............ *C10L 1/233* (2013.01); *C07D 265/36* (2013.01); *C10L 10/10* (2013.01); *C10L 2270/023* (2013.01); *C10L 2290/24* (2013.01)

(58) Field of Classification Search
CPC .... C10L 1/233; C10L 10/10; C10L 2270/023; C10L 2290/24; C07D 265/36
See application file for complete search history.

(56) References Cited

U.S. PATENT DOCUMENTS

| 4,288,589 | A | 9/1981 | Loew et al. |
| 4,861,914 | A | 8/1989 | Weidig et al. |
| 8,222,417 | B2 | 7/2012 | Suzuki et al. |
| 2005/0261244 | A1 | 11/2005 | Tuerdi et al. |
| 2006/0123696 | A1 | 6/2006 | Gaughan et al. |
| 2008/0064871 | A1 | 3/2008 | Hirata et al. |
| 2009/0094887 | A1 | 4/2009 | Calvert et al. |

FOREIGN PATENT DOCUMENTS

| CN | 105272904 A | 4/2019 |
| EP | 2172453 A1 | 4/2010 |
| EP | 3205701 A1 | 8/2017 |
| EP | 3205703 A1 | 8/2017 |
| GB | 1013572 | * 12/1965 |
| GB | 2026524 A | 2/1980 |
| JP | H04247017 A | 9/1992 |
| KR | 20120102381 A | 9/2012 |
| WO | 2009001817 A1 | 12/2008 |
| WO | 2011048112 A1 | 4/2011 |

(Continued)

OTHER PUBLICATIONS

Perry, B. et al. "Achieving multi-isofrom-PI3K inhibition in a series of substituted 3,4-dihydro-2H-benzo[1,4] oxazines." Bioorg Med Chem Lett. 2008, 18, 16, p. 4700-4704.
Dugar, S. et al. "A Concise and Efficient Synthesis of Substituted Morpholines." Synthesis. 2014, 47, 5, p. 712-720.
International Search Report and Written Opinion of International Application No. PCT/EP2018/086022, dated Apr. 10, 2019.
Coudert, G. et al. "A new synthesis of 3,4-dihydro-2H-1,4-benzoxazines using solid-liquid phase-transfer catalysis." Synthesis Georg Thieme Verlag. 1979, 7, p. 541-543.
Kotha, S. "Synthesis and Reactions of 3,4-dihydro-2H-1,4-benzoxazine Derivatives." Heterocycles. 1994, 38, p. 5-8.

(Continued)

*Primary Examiner* — Cephia D Toomer
(74) *Attorney, Agent, or Firm* — McDonnell Boehnen Hulbert & Berghoff LLP

(57) ABSTRACT

A method for preparing a substituted fuel additive d is provided. The method comprises carrying out the following reaction: (a) (b) (d), The fuel additive d may be used as an octane-boosting additive in a fuel for a spark-ignition internal combustion engine.

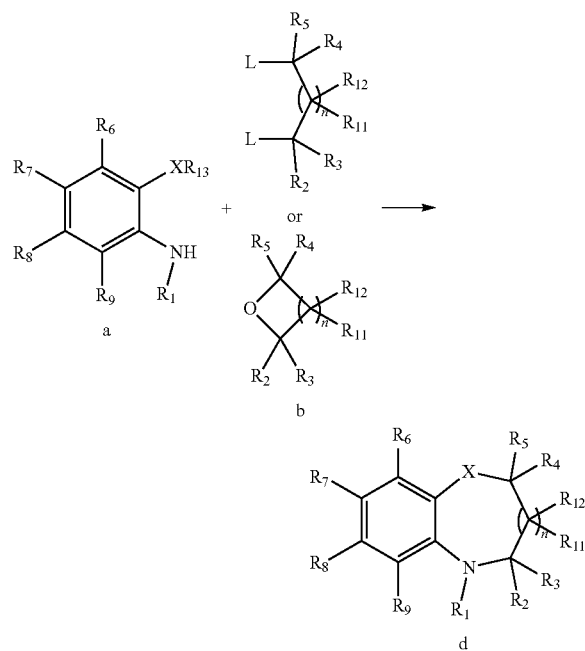

17 Claims, No Drawings

(56) References Cited

FOREIGN PATENT DOCUMENTS

| WO | 2011103460 | A1 | 8/2011 |
| WO | 2012009678 | A1 | 1/2012 |
| WO | 2014047390 | A1 | 3/2014 |
| WO | 2015063694 | A1 | 5/2015 |
| WO | 2017108723 | A2 | 6/2017 |
| WO | 2017137518 | A1 | 8/2017 |
| WO | 2017142833 | A1 | 8/2017 |

OTHER PUBLICATIONS

Hernandez-Olmos, V. et al. "N-Substituted Phenoxazine and Acridone Derivatives: Structure-Activity Relationships of Potent P2X4 Receptor Antagonists." J. Med. Chem. 2012, 55, 22, p. 9576-9588.

Bunce, R.A. et al. "Tetrahydro-1,5-benzoxazepines and tetrahydro-1H-1,5-benzodiazepines by a tandem reduction-reductive amination reaction." J. Heterocyclic Chem. 2004, 41, 6, p. 963-970.

Shadyro, O.I. et al. "Synthesis and Antiviral Activity of N-Acyl Derivatives of 4,6-Di-(tert-butyl)-2-aminophenol." Pharmaceutical Chemistry Journal 2003, 37, p. 399-401.

International Search Report and Written Opinion for International Application No. PCT/EP2018/086023, dated Jul. 4, 2019.

International Search Report and Written Opinion for International Application No. PCT/EP2018/086027, dated May 10, 2019.

Filippou, P.S. et al. "Regulation of the *Escherichia coli* AtoSC two component system by synthetic biologically active 5;7;8-trimethyl-1;4-benzoxazine analogues." Bioorgan Med Chem. 2011, 19, 16, p. 5061-5070.

Ramesh, C. et al. "A simple and facile route for the synthesis of 2H-1,4-benzoxazin-3-(4H)-ones via reductive cyclization of 2-(2-nitrophenoxy)acetonitrile adducts in the presence of Fe/acetic acid." Tetrahedron. 2011, 67, 6, p. 1187-1192.

Reddy, Ch. R. et al. "Reductive N-alkylation of aromatic amines and nitro compounds with nitriles using polymethylhydrosiloxane." Tetrahedron Let. 2007, 48, 15, p. 2765-2768.

International Search Report and Written Opinion for International Application No. PCT/EP2018/086025, dated Jun. 6, 2019.

Bartsch, H. et al. "Synthese und Reaktivitat von 2- und 3-hydroxylierten Dihydro-1,4-Benzoxazinen." Monatshefte für Chemie. 1997, 110, p. 267-278.

Mizar, P. et al. "Synthesis of substituted 4-(3-alkyl-1,2,4-oxadiazol-5-ylmethyl)-3,4-dihydro-2H-1,4-benzoxazines and 4-(1H-benzimidazol-2-ylmethyl) 3,4-dihydro-2H-1,4-benzoxazines" Tetrahedron Let. 2006, 47, 44, p. 7823-7826.

Fu, Y. et al. "Simple and efficient synthesis of novel N-dichloroacetyl-3,4-dihydro-2H-1,4-benzoxazines." Heterocycl Commun. 2012, 18, 3, p. 143-146.

International Search Report and Written Opinion for International Application No. PCT/EP2018/086024, dated Jun. 6, 2019.

Knorr, L. "Synthesen in der »Oxazinreihe«." Ber. Dtsch. Chem. Ges. 1889, 22, p. 2081-2099.

Calderone, V. et al. "Structural modifications of benzanilide derivatives, effictive potassium channel openers. X." Eur. J. Med. Chem. 2006, 41(12), p. 1421-1429.

Liu, Y. et al. "Concise synthesis of 3,4-dihydro-1,4-benzoxazines by three-component reactions of acyl chlorides, o-aminophenols and 1,2-dichloroethane." Tetrahedron 2018, 74(27), p. 3691-3696.

Huerta, G. et al. "Facile Synthesis of Aminoalcohols by Ring Opening of Epoxides Under Solvent Free Conditions." Synthetic Commun. 2004, 34(13), p. 2393-2406.

Woydowski, K. "Optically Active Heterocycles through Ring Transformations on Oxirane3-carboxylate Derivatives." Sel. Org. React. Database (SORD). 1999. See CASREACT abstract accession No. 161 :698073.

Gao, S. et al. "Synthesis and crystal structure of N-dichloroacetyl-3,4-dihydro-3-methyl-6-chloro-2H-1,4-benzoxazine". Journal of Chemistry. 2015, 2015, Article ID 268306, p. 1-5.

Yang, J. et al. "Synthesis, anti-cancer evaluation of benzenesulfoamide derivates as potent tubulin-targeting agents." Eur. J. Med. Chem. 2016, 122, p. 488-496.

Shadyro, O.I. et al. "Synthesis and Antiviral Activity of N-Acyl Derivatives of 4,6-Di-(tert-butyl)-2-aminophenol." Pharmaceutical Chemistry Journal. 2002, 36(8), p. 410-412.

* cited by examiner

METHODS FOR PREPARING FUEL ADDITIVES

This application is a national stage application under 35 U.S.C. § 371 of International Application No. PCT/EP2018/086024, filed Dec. 19, 2018, which claims priority to Great Britain Application No. 1721961.9, filed Dec. 27, 2017, the disclosures of which are explicitly incorporated by reference herein.

FIELD OF THE INVENTION

This invention relates to methods for preparing octane-boosting additives for use in a fuel for a spark-ignition internal combustion engine. In particular, the invention relates to methods for preparing octane-boosting fuel additives that are derivatives of benzo[1,4]oxazines and 1,5-benzoxazepines. The invention further relates to methods for preparing fuels for a spark-ignition internal combustion engine comprising the fuel additives.

BACKGROUND OF THE INVENTION

Spark-ignition internal combustion engines are widely used for power, both domestically and in industry. For instance, spark-ignition internal combustion engines are commonly used to power vehicles, such as passenger cars, in the automotive industry.

Fuels for a spark-ignition internal combustion engine (generally gasoline fuels) typically contain a number of additives to improve the properties of the fuel.

One class of fuel additives is octane-improving additives. These additives increase the octane number of the fuel which is desirable for combatting problems associated with pre-ignition, such as knocking. Additisation of a fuel with an octane improver may be carried out by refineries or other suppliers, e.g. fuel terminals or bulk fuel blenders, so that the fuel meets applicable fuel specifications when the base fuel octane number is otherwise too low.

Organometallic compounds, comprising e.g. iron, lead or manganese, are well-known octane improvers, with tetra-ethyl lead (TEL) having been extensively used as a highly effective octane improver. However, TEL and other organo-metallic compounds are generally now only used in fuels in small amounts, if at all, as they can be toxic, damaging to the engine and damaging to the environment.

Octane improvers which are not based on metals include oxygenates (e.g. ethers and alcohols) and aromatic amines. However, these additives also suffer from various drawbacks. For instance, N-methyl aniline (NMA), an aromatic amine, must be used at a relatively high treat rate (1.5 to 2% weight additive/weight base fuel) to have a significant effect on the octane number of the fuel. NMA can also be toxic. Oxygenates give a reduction in energy density in the fuel and, as with NMA, have to be added at high treat rates, potentially causing compatibility problems with fuel storage, fuel lines, seals and other engine components.

Recently, a new class of octane-boosting additive has been discovered. These octane-boosting additives are derivatives of benzo[1,4]oxazines and 1,5-benzoxazepines, and show great promise due to their non-metallic nature, their low oxygenate content, and their efficacy at low treat rates (see WO 2017/137518). Preferred octane-boosting additives in this class are substituted on one or more of the carbons forming part of the aromatic or heterocyclic ring.

Synthesis routes currently reported in the literature provide various descriptions of how benzoxazines may be prepared on a relatively small scale (hundreds of mg to up to 100 kg scale). For example, US 2008/064871—which relates to compounds for the treatment or prophylaxis of diseases relating to uric acid, such as gout—discloses the preparation of benzoxazine-derived compounds. Synthesis routes are also disclosed in Knorr: Synthesen in der «Oxaz-inreihe» (Ber. Dtsch. Chem. Ges., 1889, 22, 2081-2099). However, there is a need for methods that are suitable for producing the new class of octane-boosting additives on an industrial scale, e.g. in an amount of from 50 to 20,000 tonnes per year, particularly those additives in which the aromatic or heterocyclic ring is substituted.

SUMMARY OF THE INVENTION

The present invention provides a method for preparing a fuel additive d having the formula:

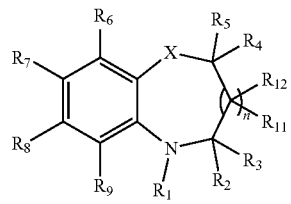

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —$NR_{10}$—, where $R_{10}$ is selected from hydrogen and alkyl groups; and n is 0 or 1, provided that at least one of $R_2$, $R_3$, $R_4$, $R_5$, $R_6$, $R_7$, $R_8$, $R_9$, $R_{11}$ and $R_{12}$ is selected from a group other than hydrogen.

The method comprises carrying out the following reaction:

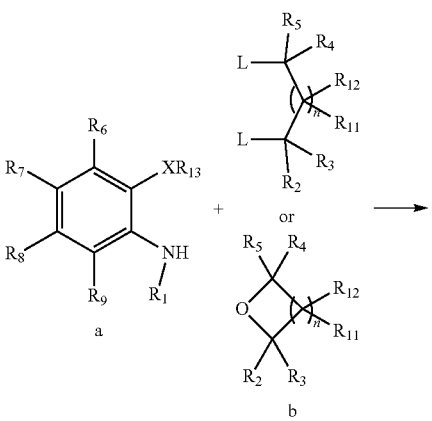

-continued

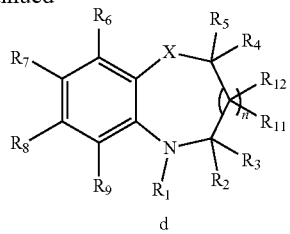

d where: $R_{13}$ is selected from hydrogen and alkyl groups; and
each L is independently selected from leaving groups, or both L groups together form the group —O—C(O)—O—.

Also provided is a fuel additive d which is obtainable by a method of the present invention.

The present invention further provides a process for preparing a fuel for a spark-ignition internal combustion engine, said process comprising:

preparing a fuel additive d using a method of the present invention; and blending the fuel additive with a base fuel.

A fuel for a spark-ignition internal combustion engine is also provided. The fuel comprises a fuel additive d of the present invention and a base fuel.

DETAILED DESCRIPTION OF THE INVENTION

Preparation Methods

The present invention provides a method for preparing a fuel additive d. According to this method, the fuel additive d is prepared by carrying out the following reaction:

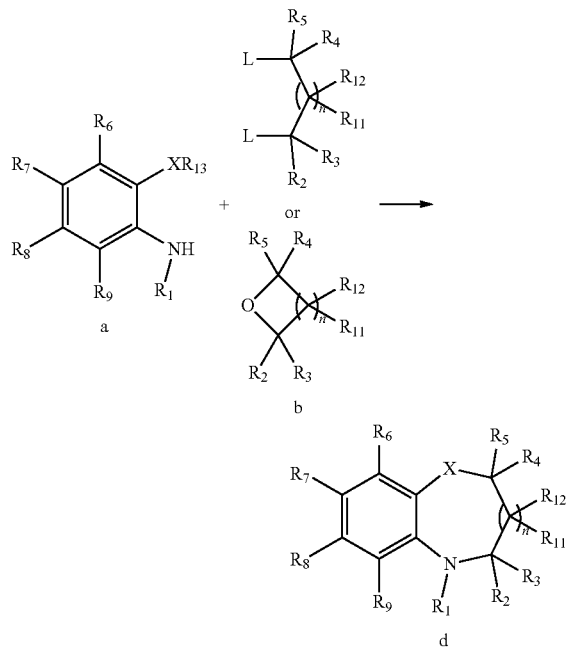

Preferably reagent b is selected from:

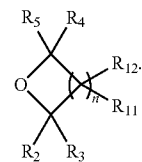

Particularly preferred are epoxide reagents, in which n=0, which readily react with starting material a to form intermediate c.

The reaction is preferably conducted using reagent b in an amount of from 0.5 to 4 molar equivalents, preferably from 0.7 to 3 molar equivalents, and more preferably from 0.8 to 2 molar equivalents as compared to starting material a.

Where reagent b contains leaving groups L, it is more preferably used in an amount of from 1 to 2 molar equivalents as compared to starting material a.

However, where reagent b does not contain leaving groups L (e.g. epoxide reagents), then it is more preferably used in an amount of from 0.8 to 1 molar equivalents as compared to starting material a. By using a slight excess of starting material a with highly reactive reagent bs, the selectivity of the reaction (for alkylation at the nitrogen, rather than the oxygen, of starting material a) is improved, and therefore also the yield.

In some embodiments, the reaction is carried out in a single step (i.e. with one set of reagents and under one set of conditions). However, in preferred embodiments, the reaction comprises the following steps:

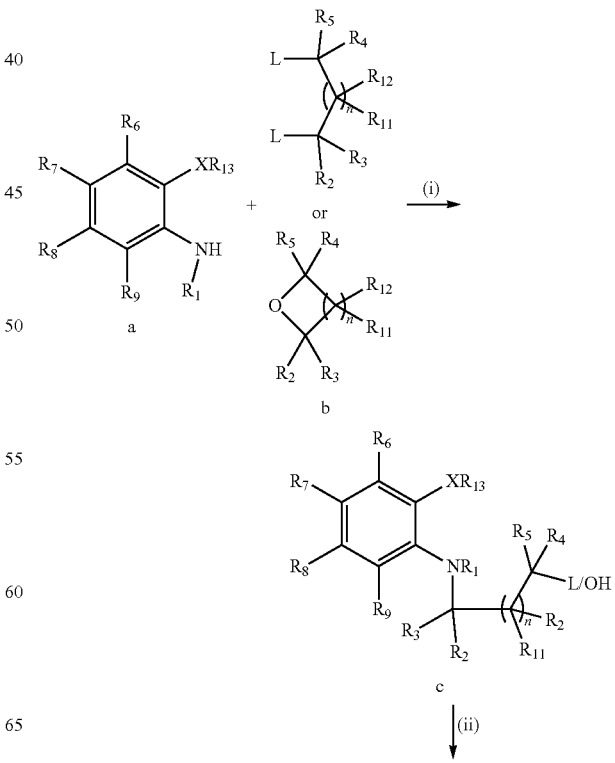

-continued

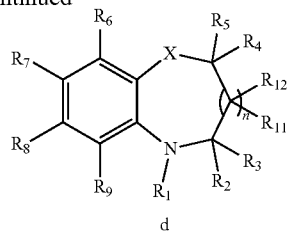

It will be appreciated that, in some instances, step (ii) will occur spontaneously on formation of intermediate c. For the purposes of the present invention, these instances are considered to be embodiments in which the reaction is carried out in a single step.

In step (i) of the method, an addition reaction is carried out, in which an alkyl group is added to an amine to form intermediate c.

In preferred embodiments, step (i) of the method is conducted in the presence of a solvent selected from aprotic solvents (e.g. tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile) and water. Particularly preferred are aprotic solvents, preferably those selected from tetrahydrofuran, acetonitrile, dimethylformamide, dimethoxyethane and dioxane. Aprotic solvents are well-known in the art as solvents which are not capable of donating protons. Aprotic solvents do not contain hydrogen atoms bound to a nitrogen or an oxygen.

Step (i) may be carried out in the presence of a basic reagent, preferably an inorganic base such as an alkali metal hydroxide (e.g. selected from sodium hydroxide and potassium hydroxide) or an alkali or alkaline earth metal carbonate (e.g. selected from sodium carbonate, sodium hydrogen carbonate, potassium carbonate, potassium hydrogen carbonate and calcium carbonate). Preferred basic reagents are alkali or alkaline earth metal carbonates, with potassium carbonate and calcium carbonate particularly preferred.

The basic reagent is preferably used in an amount of from 0.8 to 5 molar equivalents, preferably from 1 to 3 molar equivalents, and more preferably from 1.05 to 2.5 molar equivalents as compared to starting material a.

A catalyst may be used in step (i). The catalyst may be an acid (e.g. p-toluene sulfonic acid or sodium hydrogen sulphite), a zeolite (e.g. zeolite Y, sodium (faujasite)) or a metal catalyst (e.g. a palladium catalyst, preferably used with a zinc oxide support).

The catalyst may be used in an amount of less than 1 molar equivalent, preferably less than 0.5 molar equivalents, and more preferably less than 0.1 molar equivalents as compared to starting material a.

In some embodiments, step (i) may be carried out in the absence of a catalyst, e.g. where reagent b is an epoxide reagent.

Step (i) is generally conducted at a temperature of greater than 40° C., preferably greater than 60° C., and more preferably greater than 80° C. Typically, the reaction will be carried out at a temperature of less than 300° C. Where reagent b is an epoxide reagent, the reaction is preferably carried out at elevated temperatures (e.g. as above), however it may also be carried out at room temperature e.g. at a temperature at least 15° C., e.g. from 18 to 30° C.

Step (i) will generally be conducted at a pressure of from 1 to 200 bar. Typically, step (i) will be carried out at ambient pressure, i.e. a pressure of approximately 1 bar. However, where reagent b is an epoxide reagent, then a pressure of from 2 to 200 bar may be used. The reaction may be conducted for a period of greater than 30 minutes, but preferably less than 6 hours, and more preferably less than 4 hours.

Examples of preferred conditions for carrying out step (i) are as follows:
Reagent b:

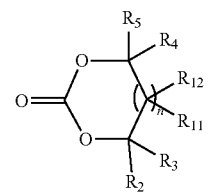

Catalyst: zeolite Y, sodium (faujasite)
Solvent: ethylene carbonate
Reagent b:

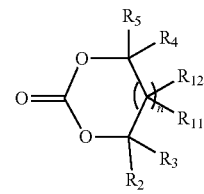

Catalyst: p-toluene sulfonic acid
Solvent: NMP
Reagent b:

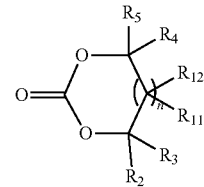

Base: potassium carbonate
Solvent: DMF
Reagent b:

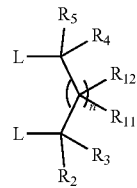

where one L is a halide and the other is —XH
Base: potassium carbonate
Solvent: water Reagent b:

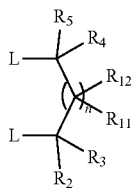

where one L is a halide and the other is —XH
Catalyst: potassium fluoride
Solvent: DMF
Reagent b:

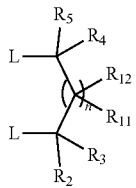

where one L is a halide and the other is —XH
Base: calcium carbonate
Solvent: water
Reagent b:

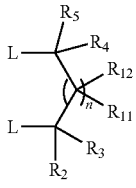

where one L is a halide and the other is —XH
Catalyst: sodium hydrogen sulfite
Solvent: water
Reagent b:

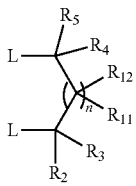

where one L is a halide and the other is —XH
Catalyst: none
Solvent: water

Reagent b:

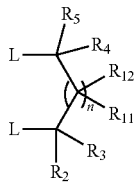

where each L is —XH
Catalyst: Pd/C, zinc oxide support
Solvent: water
Reagent b:

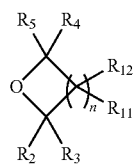

where n=0
Catalyst: none
Solvent: tetrahydrofuran, dimethoxyethane or dioxane

In step (ii) of the method, a ring closing reaction is conducted on intermediate c to form octane-boosting fuel additive d.

In some embodiments, step (ii) may be conducted in the presence of a hydrogen halide, preferably hydrogen bromide or hydrogen chloride. This is particularly preferred where a hydroxy group is present in intermediate c. The hydrogen halide is preferably in the form of an aqueous solution, e.g. containing greater than 20%, preferably greater than 40% and preferably greater than 50% by weight of the hydrogen halide.

A molar excess of hydrogen halide is preferably used, for instance by using hydrogen halide in an amount of at least 5 molar equivalents, preferably at least 10 molar equivalents, and more preferably at least 15 molar equivalents as compared to intermediate c.

In these embodiments, step (ii) may be conducted at a temperature of greater than 60° C., preferably greater than 70° C., and more preferably greater than 80° C. In these embodiments, step (ii) may be conducted at ambient pressure, i.e. approximately 1 bar.

The reaction with the hydrogen halide may be conducted for a period of greater than 1 hour, preferably greater than 2 hours, but preferably less than 5 hours.

The reaction with the hydrogen halide in step (ii) is preferably quenched using a base, for instance using an inorganic base such as an alkali metal hydroxide (e.g. sodium hydroxide or potassium hydroxide) or aqueous ammonia.

In other embodiments, step (ii) may be carried out in the presence of a base. For instance, the base may be selected from:
  inorganic bases, preferably from alkali metal hydroxides (e.g. from sodium hydroxide and potassium hydroxide) and alkali metal carbonates (e.g. from sodium bicarbonate, sodium carbonate, potassium bicarbonate and potassium carbonate), and more preferably from alkali metal hydroxides such as sodium hydroxide; and
  organic bases, more preferably from nitrogen-containing organic bases, such as from trimethylamine, diisopropylethylamine and 1,8-diazabicyclo[5.4.0]undec-7-ene.

The base is preferably used in an amount of from 0.8 to 5 molar equivalents, preferably from 1 to 3 molar equivalents, and more preferably from 1.05 to 2.5 molar equivalents as compared to intermediate c.

In these embodiments, step (ii) may be carried out in the presence of an inorganic base and:
- an aprotic solvent, preferably selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, and more preferably from tetrahydrofuran, acetonitrile, dimethoxyethane and dioxane, and more preferably selected from tetrahydrofuran; or
- a chlorinated solvent, preferably selected from trichloromethane and dichloroethane, wherein a phase-transfer reagent, preferably a quaternary ammonium salt such as a tetraalkylammonium halide salt, e.g. butyltriethylammonium chloride, is preferably used with the chlorinated solvent.

In these embodiments, step (ii) may be carried out in the presence of an organic base and an aprotic solvent, preferably selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, and more preferably from dimethylformamide, N-methyl-2-pyrrolidone, dimethyl sulfoxide, tetrahydrofuran, ethyl acetate and sulfolane.

In these embodiments, step (ii) may be carried out at a temperature of greater than 40° C., preferably greater than 50° C., and more preferably greater than 60° C. In some instances, the reaction is carried out under reflux.

In these embodiments, step (ii) will generally be carried out at ambient pressure, i.e. at a pressure of approximately 1 bar.

In these embodiments, the reaction may be conducted for a period of greater than 30 minutes, but preferably less than 10 hours, and more preferably less than 8 hours.

In other embodiments, step (ii) may be conducted in the presence of a trihydrocarbyl phosphine (e.g. a triaryl phosphine or a trialkyl phosphine, such as triphenyl phosphine or tributyl phosphine), and an azo compound (e.g. a dialkyl azodicarboxylate, such as diisopropyl azodicarboxylate). This reaction is known as a Mitsunobu reaction.

The trihydrocarbyl phosphine, e.g. triaryl phosphine or trialkyl phosphine, will typically be used in an amount of from 0.8 to 4 molar equivalents, preferably from 0.9 to 2 molar equivalents, and more preferably from 1 to 1.5 molar equivalents as compared to intermediate c. The azo compound, e.g. a dialkyl azodicarboxylate, will typically be used in an amount of from 0.8 to 1.25 molar equivalents as compared to the triaryl phosphine or trialkyl phosphine (or other trihydrocarbyl phosphine).

However, in some embodiments, the reaction may be carried out as a catalytic Mitsunobu reaction. In these embodiments, a metal catalyst may be used to enable the azo compound to also be used in catalytic amounts, e.g. from 0.01 to 0.5 molar equivalents, and preferably from 0.025 to 0.3 molar equivalents, and more preferably from 0.05 to 0.2 molar equivalents as compared to intermediate c.

Suitable metal catalysts include iron catalysts (e.g. iron phthalocyanine). The metal catalyst is preferably used in combination with a molecular sieve (e.g. a zeolite, preferably having a pore size of 5 Å). The metal catalyst may be used in an amount of from 0.01 to 0.5 molar equivalents, and preferably from 0.025 to 0.3 molar equivalents, and more preferably from 0.05 to 0.2 molar equivalents as compared to intermediate c.

Where a catalytic Mitsunobu reaction is carried out, the azo compound preferably has an aromatic group, e.g. a 3,5-dichlorophenyl group, directly bonded to one of the nitrogen atoms in the azo group. The other nitrogen of the azo group is preferably bonded to an alkyl carboxylate group, e.g. —$CO_2$Et.

Where a Mitsunobu reaction is carried out, a silane may be present such as phenyl silane. The silane will typically be used in an amount of from 0.8 to 3 molar equivalents, preferably from 0.9 to 2 molar equivalents, and more preferably from 1 to 1.5 molar equivalents as compared to intermediate c. The use of a silane is particularly preferred where a catalytic Mitsunobu reaction is carried out.

Where a Mitsunobu reaction is carried out, step (ii) is preferably conducted in the presence of an aprotic solvent, preferably selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, and more preferably from tetrahydrofuran, acetonitrile, dimethoxyethane and dioxane.

Where a Mitsunobu reaction is carried out, step (ii) is typically conducted at ambient temperature, i.e. at a temperature of from 15 to 25° C. Higher temperatures may also be used, e.g. up to 80° C., particularly where the reaction is a catalytic Mitsunobu reaction.

Where a Mitsunobu reaction is carried out, step (ii) is preferably conducted at ambient pressure, i.e. at a pressure of approximately 1 bar.

Where a Mitsunobu reaction is carried out, the reaction will typically be conducted for a period of greater than 15 minutes, but less than 4 hours, and more preferably less than 2 hours. Catalytic Mitsunobu reactions may be carried out for longer, e.g. up to 24 or even 48 hours.

In other embodiments, the reaction comprises the following steps:

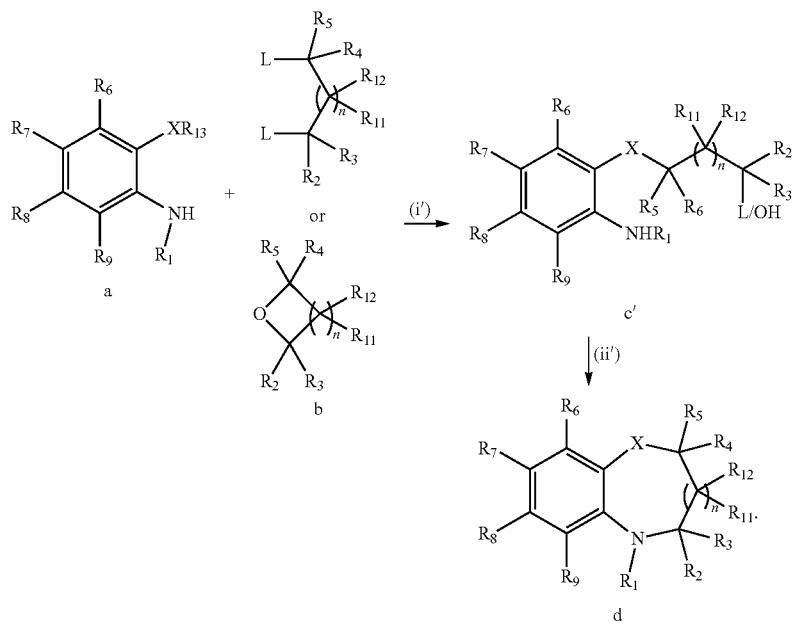

It will be appreciated that, in some instances, step (ii') will occur spontaneously on formation of intermediate c'. For the purposes of the present invention, these instances are considered to be embodiments in which the reaction is carried out in a single step. In step (i') of the method, an addition reaction is carried out, in which an alkyl group is added to a hydroxy group to form intermediate c'.

In preferred embodiments, step (i') of the method is conducted in the presence of a base, preferably an inorganic base, such as an alkali metal hydroxide (e.g. selected from sodium hydroxide and potassium hydroxide) and alkali metal carbonates (e.g. selected from sodium bicarbonate, sodium carbonate, potassium bicarbonate and potassium carbonate). Step (i') is preferably conducted in the presence of an alkali metal carbonate, preferably selected from sodium carbonate or potassium carbonate.

The base is preferably used in an amount of from 0.8 to 5 molar equivalents, preferably from 1 to 3 molar equivalents, and more preferably from 1.05 to 2.5 molar equivalents as compared to starting material a.

Step (i') of the method may be conducted in an aprotic solvent, preferably selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile, and more preferably from dimethylformamide, N-methyl-2-pyrrolidone, dimethyl sulfoxide, tetrahydrofuran, ethyl acetate and sulfolane.

In these embodiments, step (i') may be carried out at a temperature of greater than 40° C., preferably greater than 50° C., and more preferably greater than 60° C. In some instances, the reaction is carried out under reflux.

Step (i') will generally be carried out at ambient pressure, i.e. at a pressure of approximately 1 bar.

The reaction may be conducted for a period of greater than 1 hour, but preferably less than 24 hours, and more preferably less than 12 hours.

In these embodiments, reagent b is preferably selected from:

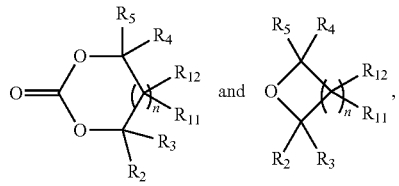

and more preferably from:

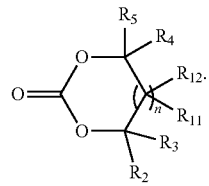

In some embodiments, step (ii') of the method may be conducted in the presence of a hydrogen halide, preferably hydrogen bromide or hydrogen chloride. This is particularly preferred where a hydroxy group is present in intermediate c. The hydrogen halide is preferably in the form of an aqueous solution, e.g. containing greater than 20%, preferably greater than 40% and preferably greater than 50% by weight of the hydrogen halide.

A molar excess of hydrogen halide is preferably used, for instance by using hydrogen halide in an amount of at least 5 molar equivalents, preferably at least 10 molar equivalents, and more preferably at least 15 molar equivalents as compared to intermediate c.

In these embodiments, step (ii') may be conducted at a temperature of greater than 60° C., preferably greater than 70° C., and more preferably greater than 80° C.

In these embodiments, step (ii') may be conducted at ambient pressure, i.e. approximately 1 bar.

In these embodiments, the reaction with the hydrogen halide may be conducted for a period of greater than 1 hour, preferably greater than 2 hours, but preferably less than 5 hours.

In these embodiments, the reaction with the hydrogen halide in step (ii') is preferably quenched using a base, for instance using an inorganic base such as an alkali metal hydroxide (e.g. sodium hydroxide or potassium hydroxide) or aqueous ammonia.

In other embodiments, step (ii') may be conducted in the presence of a metal catalyst. It will be appreciated that metal catalysts are metal-containing catalysts and, as such, they may contain non-metallic elements.

Suitable metal catalysts include those selected from palladium (e.g. Pd/C, PdO, Pd/Al$_2$O$_3$, Pd/C/ZnO or PdCl$_2$(PPh$_3$)$_2$), nickel (e.g. in the presence of aluminium such as in Raney nickel or Ni—SiO$_2$/Al$_2$O$_3$), cobalt (e.g. in the presence of aluminium such as in Raney cobalt), platinum (e.g. Pt/C, PtO$_2$, Pt/Al$_2$O$_3$, Pt/C/Cu, Pt/C/Fe, PtSiO$_2$ or Pt/CN), ruthenium (e.g. Ru/C, RuO$_2$, Ru/Al$_2$O$_3$, RuCl$_2$(PPh$_3$)$_3$, Cp*RuCl(PPh$_3$)$_2$, Cp*RuCl(COD), (Cp*RuCl)$_4$ or CpRuCl(PPh$_3$)$_2$), iridium (e.g. Ir/C or [Cp*IrCl$_2$]$_2$), rhodium (e.g. Rh/C, Rh$_2$O$_3$, Rh/Al$_2$O$_3$, [Rh(COD)Cl]$_2$, (PPh$_3$)$_3$RhCl or RhCl(CO)(PPh$_3$)$_2$) and copper (e.g. in the presence of aluminium such as in Raney Cu, CuO/ZnO, CuO/Al$_2$O$_3$/MnO or Cu$_2$Cr$_2$O$_5$) catalysts. As is standard in the art, Cp* represents the ligand 1,2,3,4,5-pentamethylcyclopentadienyl, Cp represents the ligand cyclopentadienyl and COD represents the ligand 1,5-cyclooctadiene.

In these embodiments, the metal catalyst may be used in an amount of up to 0.5 molar equivalents as compared to intermediate c', for instance from 0.001 to 0.5, preferably from 0.005 to 0.4, and more preferably from 0.01 to 0.3 equivalents as compared to intermediate c'.

In these embodiments, the reaction is preferably carried out at a temperature of at least 100° C., such as a temperature of from 100 to 250° C.

The reaction in the presence of a metal catalyst in step (ii') may be carried out in the presence of: (1) a basic catalyst; (2) no further components; (3) a hydrogen source, or (4) a reaction additive. Each of these options is described in greater detail below:

(1) Basic Catalyst

Particularly suitable metal catalysts where a basic catalyst is used include ruthenium (e.g. in the form of RuCl$_2$(PPh$_3$)$_3$) and iridium (e.g. [Cp*IrCl$_2$]$_2$) catalysts.

Preferred basic catalysts include inorganic bases, such as those selected from alkali metal carbonates (e.g. alkali metal carbonates such as sodium carbonate, sodium bicarbonate, potassium carbonate and potassium bicarbonate) and alkali metal alkoxides (e.g. alkali metal tert-butoxides such as sodium tert-butoxide or potassium tert-butoxide). Alkali metal oxides are believed to give very high yields.

The base may be used in an amount of from 0.005 to 0.5 molar equivalents, preferably from 0.01 to 0.3 molar equivalents, and more preferably from 0.05 to 0.2 molar equivalents as compared to starting material c'.

The reaction may be carried out in the presence of a solvent system, such as an aprotic solvent system. It will be appreciated that trace amounts (e.g. less than 5%, less than 3% or less than 1% by volume of the aprotic solvent system) of protic solvents may be present, e.g. as a result of the catalyst or base being prepared in a protic solvent such as water.

The aprotic solvent system preferably comprises an aromatic solvent (e.g. a solvent selected from toluene, benzene, xylenes, trimethyl benzenes such as mesitylene, diphenyl ether, naphthalene, methyl-substituted naphthalenes (i.e. 1- and 2-methyl naphthalene) and anisole). The aromatic solvent may be present in the aprotic solvent system in an amount of at least 30%, preferably at least 40%, and more preferably at least 50%, by weight. In embodiments, the aromatic solvent is the only solvent that is used, i.e. the aprotic solvent system consists of the aromatic solvent.

The reaction will generally be carried out substantially in the absence of hydrogen gas, e.g. at a level of less than 10 ppm and preferably less than 1 ppm by volume. Preferably, no further reaction materials (e.g. reagents or catalysts) beyond material c', the metal catalyst, the basic catalyst and, optionally, the solvent system are present.

The reaction is preferably carried out at a temperature of from 100 to 200° C., preferably from 100 to 180° C., and more preferably from 100 to 150° C. The reaction will generally be carried out at ambient pressure, i.e. at a pressure of approximately 1 bar.

The reaction may be conducted for a period of greater than 2 hours, and preferably greater than 12 hours. Typically, the reaction will be carried out for up to 48 hours.

(2) No Further Components

In some particularly preferred embodiments, step (ii') may be carried out in the presence of a metal catalyst and, optionally, a solvent system.

The reaction will generally be carried out substantially in the absence of hydrogen gas, e.g. at a level of less than 10 ppm and preferably less than 1 ppm by volume. Preferably, no further reaction materials (e.g. reagents or catalysts) beyond material c', the metal catalyst and, optionally, the solvent system are present.

Suitable metal catalysts include ruthenium (e.g. as RuCl$_2$(PPh$_3$)$_3$, Cp*RuCl(PPh$_3$)$_2$, Cp*RuCl(COD), (Cp*RuCl)$_4$ or CpRuCl(PPh$_3$)$_2$), palladium (e.g. PdCl$_2$(PPh$_3$)$_2$), rhodium (e.g. [Rh(COD)Cl]$_2$, (PPh$_3$)$_3$RhCl or RhCl(CO)(PPh$_3$)$_2$) and nickel (e.g. Raney nickel) catalysts. Nickel catalysts are believed to be particularly suitable, with Raney nickel in particular providing a high yield.

The reaction is optionally carried out in the presence of a solvent system. However, in some embodiments, it is preferred to carry out the reaction using solely material c' as the solvent. This system is chemically very efficient and is capable of producing the compound d in large yields.

Solvent systems that may be used include aprotic solvent systems. It will be appreciated that trace amounts (e.g. less than 5%, less than 3% or less than 1% by volume of the aprotic solvent system) of protic solvents may be present during the reaction, e.g. as a result of the catalyst being prepared as a catalyst-in-water slurry.

The aprotic solvent system preferably may comprise an aromatic solvent, such as a solvent selected from toluene, benzene, xylenes, trimethyl benzenes such as mesitylene, diphenyl ether, napththalene, methyl-substituted naphthalenes and anisole. Mesitylene is particularly suitable, delivering high yields of the compound d.

The aromatic solvent may be present in the aprotic solvent system in an amount of at least 30%, preferably at least 40%, and more preferably at least 50%, by weight. In preferred embodiments, the aromatic solvent is the only solvent that is used, i.e. the aprotic solvent system consists of the aromatic solvent.

The aprotic solvent system may comprise a non-aromatic solvent. Preferred non-aromatic solvents are selected from heterocyclic solvents, such as from N-methyl-2-pyrrolidone, tetrahydrofuran and 1,4-dioxane. Other suitable aprotic non-aromatic solvents include dimethylacetamide. The non-aromatic solvent may be used alone or in combination with an aromatic solvent.

The solvent system may be used in an amount of up to 10 volume equivalents, for instance from 1 to 10 volume equivalents, preferably from 1.5 to 5 volume equivalents, and more preferably from 2 to 3 volume equivalents, as compared to material c'.

The reaction is preferably carried out at a temperature of from 100 to 200° C., preferably from 115 to 180° C., and more preferably from 130 to 160° C. The reaction will generally be carried out at ambient pressure, i.e. at a pressure of approximately 1 bar.

The reaction may be conducted for a period of greater than 2 hours, preferably greater than 10 hours, for instance greater than 20 hours. Typically, the reaction will be carried out for up to 30 hours. These values represent the period of time over which the reaction is out at a temperature of at least 100° C.

(3) Hydrogen Source

In some preferred embodiments, step (ii') may be carried out in the presence of a metal catalyst, a hydrogen source and an aprotic solvent system.

The reaction may be carried out in the presence of a wide range of metal catalysts. Suitable metal catalysts include those selected from palladium (e.g. Pd/C, PdO, Pd/Al$_2$O$_3$, Pd/C/ZnO or PdCl$_2$(PPh$_3$)$_2$), nickel (e.g. in the presence of aluminium such as in Raney nickel or Ni—SiO$_2$/Al$_2$O$_3$), cobalt (e.g. in the presence of aluminium such as in Raney cobalt), platinum (e.g. Pt/C, Pt/Al$_2$O$_3$, Pt/C/Cu, Pt/C/Fe, PtSiO$_2$ or Pt/CN), ruthenium (e.g. Ru/C or Ru/Al$_2$O$_3$), iridium (e.g. Ir/C), rhodium (e.g. Rh/C, Rh/Al$_2$O$_3$, [Rh(COD)Cl]$_2$, (PPh$_3$)$_3$RhCl or RhCl(CO)(PPh$_3$)$_2$), copper (e.g. in the presence of aluminium such as in Raney Cu, CuO/ZnO, CuO/Al$_2$O$_3$/MnO or Cu$_2$Cr$_2$O$_5$) and ruthenium (e.g. Cp*RuCl(PPh$_3$)$_2$, Cp*RuCl(COD), (Cp*RuCl)$_4$ or CpRuCl(PPh$_3$)$_2$) catalysts. Nickel catalysts, in particular Ni—SiO$_2$/Al$_2$O$_3$, are particularly suitable since these catalysts are believed to give high yields of the compound d.

The reaction is preferably carried out as a heterogeneous catalyst reaction. Heterogeneous catalysis reactions involve the use of a catalyst in a different phase from the reactants. In this embodiment, the reaction is preferably carried out with a solid catalyst in a liquid reagent phase. Thus, preferred metal catalysts are supported, e.g. on insoluble media, such as on carbon, alumina or silica. The metal catalyst may be used in the form of a slurry or in the form of a fixed bed catalyst.

The reaction is carried out in the presence of a hydrogen source. The hydrogen source is preferably hydrogen gas, for instance at a pressure of from 1 to 50 bar, preferably from 3 to 30 bar, and more preferably from 5 to 15 bar. Though less preferred, hydrogen transfer reagents may also be used as the hydrogen source, e.g. formic acid, sodium formate or ammonium formate.

The reaction is carried out in the presence of an aprotic solvent system. It will be appreciated that trace amounts (e.g. less than 5%, less than 3% or less than 1% by volume of the aprotic solvent system) of protic solvents may be present during the reaction, e.g. as a result of the catalyst being prepared as a catalyst-in-water slurry.

The aprotic solvent system preferably comprises an aromatic solvent, such as a solvent selected from toluene, benzene, xylenes, trimethyl benzenes such as mesitylene, diphenyl ether, naphthalene, methyl-substituted naphthalenes and anisole. Mesitylene is particularly suitable, delivering high yields of the compound d.

The aromatic solvent may be present in the aprotic solvent system in an amount of at least 30%, preferably at least 40%, and more preferably at least 50%, by weight. In embodiments, the aromatic solvent is the only solvent that is used, i.e. the aprotic solvent system consists of the aromatic solvent.

The aprotic solvent system may also comprise a non-aromatic solvent. Preferred non-aromatic solvents are selected from heterocyclic solvents, such as from N-methyl-2-pyrrolidone, tetrahydrofuran and 1,4-dioxane. Other suitable aprotic non-aromatic solvents include dimethylacetamide. The non-aromatic solvent is preferably used in combination with an aromatic solvent.

Preferably, no further reaction materials (e.g. reagents or catalysts) beyond material c', the metal catalyst, the hydrogen source and, optionally, the aprotic solvent system are present.

The reaction is preferably carried out at a temperature of at a temperature of from 100 to 250° C., preferably from 130 to 230° C., and more preferably from 150 to 200° C.

The reaction will generally be carried out at just one temperature. However, in some embodiments, the reaction may be brought up to temperature over a period of up to 3 hours, preferably up to 2 hours, and more preferably up to 1.5 hours. For instance, the reaction may be carried out at a temperature of from 40 to 100° C. for a period of to 3 hours, preferably up to 2 hours, and more preferably up to 1.5 hours, before the reaction is taken up to full temperature.

The reaction may be conducted for a period of greater than 2 hours, preferably greater than 4 hours. Typically, the reaction will be carried out for up to 24 hours. These values represent the period of time over which the reaction is out at a temperature of at least 100° C.

(4) Reaction Additive.

In some embodiments, step (ii') may be carried out in the presence of a metal catalyst and a reaction additive.

Suitable metal catalysts include those selected from palladium (e.g. Pd/C or PdO), platinum (e.g. Pt/C or PtO$_2$), ruthenium (e.g. Ru/C or RuO$_2$) and rhodium (e.g. Rh/C or Rh$_2$O$_3$) catalysts. Palladium catalysts are particularly suitable, since they are believed to give the compound din high yields.

The reaction is carried out in the presence of a reaction additive. Suitable reaction additives include metal oxides and inorganic basis. Preferred metal oxides include zinc oxide. Preferred inorganic bases include such as alkali metal hydroxides, alkali metal carbonates (including alkali metal hydrogen carbonates), alkali metal phosphates and alkali metal formates. Sodium or potassium will typically be used as the alkali metal. Preferred inorganic bases include sodium formate. Metal oxides such as zinc oxide are preferred when an aqueous solvent system is used, whereas alkali metal bases such as sodium formate are preferred for use with aprotic solvent systems.

The reaction additive may be used in an amount of up to 5 molar equivalents, for instance from 0.1 to 5 molar equivalents, preferably from 0.5 to 4 molar equivalents, and more preferably from 1 to 3 molar equivalents, as compared to material c'. It will be appreciated that the reaction additive may be used in over-stoichiometric amounts and will typically be consumed in the reaction as a reagent.

The reaction may be carried out in the presence of a protic or an aprotic solvent system, though aprotic solvent systems are generally preferred. It will be appreciated that trace amounts (e.g. less than 5%, less than 3% or less than 1% by volume of the aprotic solvent system) of protic solvents may be present during the reaction, e.g. as a result of the catalyst or reaction additive being prepared in a protic solvent such as water.

Protic solvents are well-known in the art as solvents which are capable of donating protons. Protic solvents typically contain hydrogen atoms directly bound to a nitrogen or an oxygen.

Protic solvent systems include aqueous, i.e. water-containing, solvent systems. In some embodiments, the aqueous solvent system may contain only water. In other embodiments, a mixture of water and an alcohol (e.g. tert-butanol) or ether (e.g. dimethoxyethane) may be used.

Suitable aprotic solvent systems preferably comprise an aromatic solvent (e.g. a solvent selected from toluene, benzene, xylenes, trimethyl benzenes such as mesitylene, diphenyl ether, naphthalene, methyl-substituted naphthalenes and anisole) or a non-aromatic solvent (e.g. N-methyl-2-pyrrolidone, tetrahydrofuran and 1,4-dioxane).

In some embodiments, an aromatic aprotic solvent, e.g. as described above, may be used in combination with a protic solvent, e.g. as described above. Toluene and tert-butanol may be used together.

The reaction will generally be carried out substantially in the absence of hydrogen gas, e.g. at a level of less than 10 ppm and preferably less than 1 ppm by volume. Preferably, no further reaction materials (e.g. reagents or catalysts) beyond material c', the metal catalyst, the reaction additive and, optionally, the solvent system are present.

The reaction is preferably carried out at a temperature of at a temperature of from 105 to 200° C., preferably from 110 to 180° C., and more preferably from 120 to 160° C. The reaction will generally be carried out at just one temperature.

The reaction will generally be carried out at ambient pressure, i.e. at a pressure of approximately 1 bar.

The reaction may be conducted for a period of greater than 6 hours, preferably greater than 12 hours. Typically, the reaction will be carried out for up to 136 hours. These values represent the period of time over which the reaction is out at a temperature of at least 100° C.

In the method of the present invention, substituent $R_{13}$ of starting material a is selected from hydrogen and alkyl groups. Preferably, $R_{13}$ is selected from hydrogen, methyl, ethyl, propyl and butyl, preferably from hydrogen and methyl, and more preferably is methyl.

Where reagent b contains leaving groups L, one of these leaving groups L is lost during step (i) or (i'), with the other lost during step (ii) or (ii'). Each L is independently selected from leaving groups or both L groups together form the group —O—C(O)—O—, a group which effectively provides two leaving groups. Suitable leaving groups include: halides (e.g. Cl, Br, I), substituted aryloxy groups (e.g. —O—Ar, where Ar is selected from nitro-substituted aryl groups such as p-nitrophenyl), sulfonates (e.g. —OSO$_2$A, where A is selected from tolyl, methyl, —CF$_3$, —CH$_2$Cl, phenyl and p-nitrophenyl) and —XH. Each L is preferably independently selected from Cl, Br and —XH.

The methods of the present invention are preferably carried out on an industrial scale. For instance, where the method of preparing fuel additive d is a batch process, the fuel additive is preferably produced in a batch quantity of greater than 100 kg, preferably greater than 150 kg, and more preferably greater than 200 kg. The method may also be carried out as a continuous process.

In order to produce the fuel additive on an industrial scale, the reaction is preferably carried out in a reactor or, where the reaction comprises sub-steps (i) and (ii) or (i') and (ii'), reactors having a capacity of at least 500 L, preferably at least 750 L, and more preferably at least 1000 L. It will be appreciated that, where the reaction comprises sub-steps, more than one (e.g. each) sub-step may be carried out in the same reactor.

Octane-Boosting Fuel Additive d

Fuel additives d that are prepared using the methods of the present invention have the following formula:

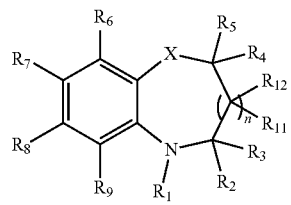

where: $R_1$ is hydrogen;

$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;

$R_6$, $R_7$, $R_8$ and $R_9$ are each independently selected from hydrogen, alkyl, alkoxy, alkoxy-alkyl, secondary amine and tertiary amine groups;

X is selected from —O— or —NR$_{10}$—, where $R_{10}$ is selected from hydrogen and alkyl groups; and n is 0 or 1, provided that at least one of $R_2$, $R_3$, $R_4$, $R_5$, $R_6$, $R_7$, $R_8$, $R_9$, $R_{11}$ and $R_{12}$ is selected from a group other than hydrogen.

Preferred substituents for the fuel additives are described below. It will be appreciated that the preferred substitution patterns also apply to the starting material a, reagent b, and intermediates c and c' from which the fuel additive d is prepared.

In some embodiments, $R_2$, $R_3$, $R_4$, $R_5$, $R_{11}$ and $R_{12}$ are each independently selected from hydrogen and alkyl groups, and preferably from hydrogen, methyl, ethyl, propyl and butyl groups. More preferably, $R_2$, $R_3$, $R_4$, $R_5$, $R_{11}$ and $R_{12}$ are each independently selected from hydrogen, methyl and ethyl, and even more preferably from hydrogen and methyl.

In some embodiments, $R_6$, $R_7$, $R_8$ and $R_9$ are each independently selected from hydrogen, alkyl and alkoxy groups, and preferably from hydrogen, methyl, ethyl, propyl, butyl, methoxy, ethoxy and propoxy groups. More preferably, $R_6$, $R_7$, $R_8$ and $R_9$ are each independently selected from hydrogen, methyl, ethyl and methoxy, and even more preferably from hydrogen, methyl and methoxy.

At least one of $R_2$, $R_3$, $R_4$, $R_5$, $R_6$, $R_7$, $R_8$, $R_9$, $R_{11}$ and $R_{12}$, and preferably at least one of $R_6$, $R_7$, $R_8$ and $R_9$, is selected from a group other than hydrogen. More preferably, at least one of $R_7$ and $R_8$ is selected from a group other than hydrogen. Alternatively stated, the octane-boosting additive is substituted in at least one of the positions represented by $R_2$, $R_3$, $R_4$, $R_5$, $R_6$, $R_7$, $R_8$, $R_9$, $R_{11}$ and $R_{12}$, preferably in at least one of the positions represented by $R_6$, $R_7$, $R_8$ and $R_9$, and more preferably in at least one of the positions represented by $R_7$ and $R_8$. It is believed that the presence of at least one group other than hydrogen may improve the solubility of the octane-boosting additives in a fuel.

Also advantageously, no more than five, preferably no more than three, and more preferably no more than two, of $R_2$, $R_3$, $R_4$, $R_5$, $R_6$, $R_7$, $R_8$, $R_9$, $R_{11}$ and $R_{12}$ are selected from a group other than hydrogen. Preferably, one or two of $R_2$, $R_3$, $R_4$, $R_5$, $R_6$, $R_7$, $R_8$, $R_9$, $R_{11}$ and $R_{12}$ are selected from a group other than hydrogen. In some embodiments, only one of $R_2$, $R_3$, $R_4$, $R_5$, $R_6$, $R_7$, $R_8$, $R_9$, $R_{11}$ and $R_{12}$ is selected from a group other than hydrogen.

It is also preferred that at least one of $R_2$ and $R_3$ is hydrogen, and more preferred that both of $R_2$ and $R_3$ are hydrogen.

In preferred embodiments, at least one of $R_4$, $R_5$, $R_7$ and $R_8$ is selected from methyl, ethyl, propyl and butyl groups and the remainder of $R_2$, $R_3$, $R_4$, $R_5$, $R_6$, $R_7$, $R_8$, $R_9$, $R_{11}$ and $R_{12}$ are hydrogen. More preferably, at least one of $R_7$ and $R_8$ are selected from methyl, ethyl, propyl and butyl groups and the remainder of $R_2$, $R_3$, $R_4$, $R_5$, $R_6$, $R_7$, $R_8$, $R_9$, $R_{11}$ and $R_{12}$ are hydrogen.

In further preferred embodiments, at least one of $R_4$, $R_5$, $R_7$ and $R_8$ is a methyl group and the remainder of $R_2$, $R_3$, $R_4$, $R_5$, $R_6$, $R_7$, $R_8$, $R_9$, $R_{11}$ and $R_{12}$ are hydrogen. More preferably, at least one of $R_7$ and $R_8$ is a methyl group and the remainder of $R_2$, $R_3$, $R_4$, $R_5$, $R_6$, $R_7$, $R_8$, $R_9$, $R_{11}$ and $R_{12}$ are hydrogen.

Preferably, X is —O— or —NR$_{10}$—, where $R_{10}$ is selected from hydrogen, methyl, ethyl, propyl and butyl groups, and preferably from hydrogen, methyl and ethyl groups. More preferably, $R_{10}$ is hydrogen. In preferred embodiments, X is —O—.

n may be 0 or 1, though it is preferred that n is 0.

Octane-boosting additives that may be used in the present invention include:

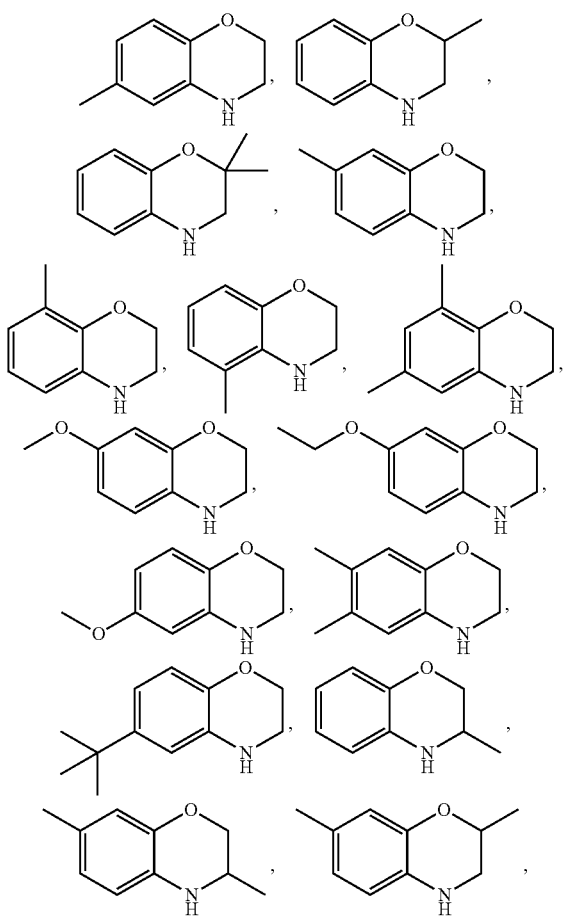

-continued

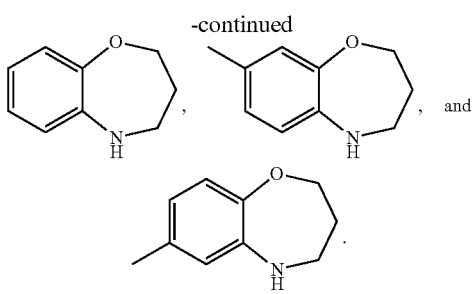

Preferred octane-boosting additives include:

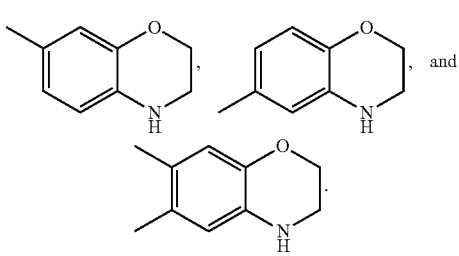

Particularly preferred is the octane-boosting additive:

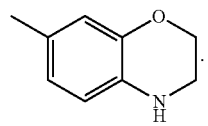

A mixture of additives may be used in the fuel composition. For instance, the fuel composition may comprise a mixture of:

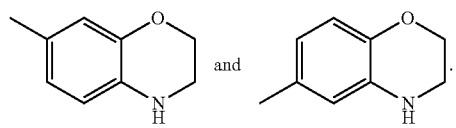

It will be appreciated that references to alkyl groups include different isomers of the alkyl group. For instance, references to propyl groups embrace n-propyl and i-propyl groups, and references to butyl embrace n-butyl, isobutyl, sec-butyl and tent-butyl groups.

Additive and Fuel Compositions

The present invention provides fuel additives d which are obtainable by a method of the present invention. Preferably, the fuel additives are obtained by a method of the present invention.

The present invention also provides a process for preparing a fuel for a spark-ignition internal combustion engine, said process comprising:

preparing a fuel additive d using a method of the present invention; and blending the fuel additive with a base fuel.

A fuel for a spark-ignition internal combustion engine is also provided. The fuel comprises a fuel additive d, obtainable and preferably obtained by a method of the present invention, and a base fuel.

Gasoline fuels (including those containing oxygenates) are typically used in spark-ignition internal combustion engines. Commensurately, the fuel composition that may be prepared according to the process of the present invention may be a gasoline fuel composition.

The fuel composition may comprise a major amount (i.e. greater than 50% by weight) of liquid fuel ("base fuel") and a minor amount (i.e. less than 50% by weight) of additive composition of the present invention. Examples of suitable liquid fuels include hydrocarbon fuels, oxygenate fuels and combinations thereof.

The fuel composition may contain the octane-boosting fuel additive d in an amount of up to 20%, preferably from 0.1% to 10%, and more preferably from 0.2% to 5% weight additive/weight base fuel. Even more preferably, the fuel composition contains the fuel additive in an amount of from 0.25% to 2%, and even more preferably still from 0.3% to 1% weight additive/weight base fuel. It will be appreciated that, when more than one octane-boosting fuel additive d is used, these values refer to the total amount of fuel additive d in the fuel.

The fuel compositions may comprise at least one other further fuel additive. Examples of such other additives that may be present in the fuel compositions include detergents, friction modifiers/anti-wear additives, corrosion inhibitors, combustion modifiers, anti-oxidants, valve seat recession additives, dehazers/demulsifiers, dyes, markers, odorants, anti-static agents, anti-microbial agents, and lubricity improvers. Further octane improvers may also be used in the fuel composition, i.e. octane improvers which do not have the structure of octane-boosting fuel additive d.

The fuel compositions are used in a spark-ignition internal combustion engine. Examples of spark-ignition internal combustion engines include direct injection spark-ignition engines and port fuel injection spark-ignition engines. The spark-ignition internal combustion engine may be used in automotive applications, e.g. in a vehicle such as a passenger car.

The invention will now be described with reference to the following non-limiting examples.

EXAMPLES

Example 1

Preparation of Intermediate c Via Route (i)

Intermediate c was prepared according to the following scheme:

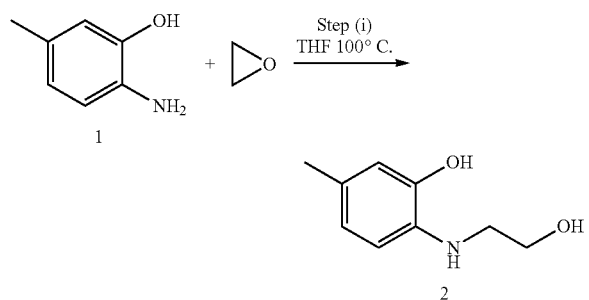

A solution of 5-methyl-2-aminophenol 1 (10.0 g, 81 mmol) and ethylene oxide (2.5 to 3.3 M solution in THF, 25 ml, ~72 mmol) was heated in an autoclave to 100° C. for 2 hours and cooled to ambient. The solvent was evaporated to dryness and the resulting solid recrystallised from ethyl acetate to give 4.4 g (32% yield) of 2 as an off white solid.

Example 2

Preparation of Octane-Boosting Fuel Additive d Via Route (ii)

Fuel additive f was prepared from intermediate c according to the following scheme:

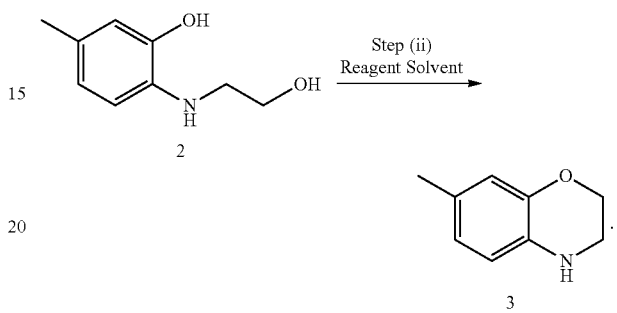

In a first experiment, the fuel additive was prepared using triphenylphosphine and diisopropyl azodicarboxylate, in the presence of a tetrahydrofuran solvent.

The compound 2 (1.0 g, 6 mmol) and triphenylphosphine (6.2 mmol) were sonicated in THF (5 ml) for 2 minutes and then a solution of DIAD (6.2 mmol) in THF (5 ml) added over 2 minutes and sonication continued for approximately 30 minutes. The reaction mixture was diluted with approximately 30 ml of hexane and decanted away from a dark oil. The solvent was evaporated and purified by column chromatography using 20 to 40% ethyl acetate/hexane. Product fractions evaporated to give 0.4 g (45% yield) of 3 as a colourless oil (measured by LCMS).

In a second experiment, the fuel additive was prepared using aqueous hydrogen bromide.

A solution of 2-((2-hydroxyethyl)amino)-5-methylphenol 2 (6.7 g, 0.04 mol) in 35 mL of concentrated hydrobromic acid 62% (0.88 mol) was stirred and refluxed for 3 hours. The reaction mixture was basified with concentrated ammonium hydroxide 28% (50 mL) and water was evaporated in vacuo. The residue was treated with ethyl acetate (200 mL), the mixture was stirred for 1 hour and then filtered. The filtrate was dried over anhydrous sodium sulfate and evaporated in vacuo to give 4.47 g (75% yield) of 3.

Example 3

Preparation of Intermediate c' Via Route (i')

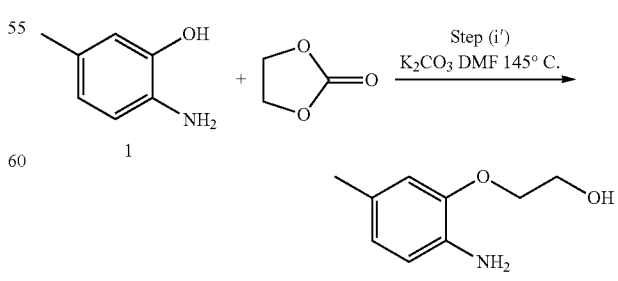

A solution of 2-amino-5-methylphenol 1 (500.0 g, 4.06 mol) and ethylene carbonate (554 g, 6.29 mol) in DMF (5 L) was treated with potassium carbonate (2244 g, 16.24 mol) and heated to 145° C. for 1 h. Once cooled to room temperature, DMF was removed under reduced pressure. The resulting residue was then partitioned between ethyl acetate (5 L) and water (4 L). The separated organic phase was washed with water (4 L) and brine (2 L) and concentrated. A further 500 g and 3×250 g of 2-amino-5-methylphenol 1 were processed to give crude product 2 (2051 g) as a dark brown oil. The crude product was purified by adding tent-butyl methyl ether (10 L) and stirred on a rotary evaporator for 20 mins. The resulting solid was collected by vacuum filtration, washed with test-butyl methyl ether (500 ml) and vacuum dried to give product 2 (596 g) as a brown solid, with a purity of 99.82% as measured by UPLC-MS (run time: 1.40 mins; solvents B) acetonitrile C) 10 mM NH$_4$HCO$_3$ at pH 10; gradient: 2-98% B with C in 1.2 mins, hold at 98% B 2% C to 1.40 min; flow rate of 0.8 ml/min at 40° C.).

The filtrate was diluted with tent-butyl methyl ether (5 L), washed with water (4.5 L), dried over sodium sulphate and concentrated. The residue (1069 g) was triturated with tert-butyl methyl ether (3 L) to give a dark brown solid (232 g). The solid was further purified by recrystallisation from isopropanol (300 ml) to give a second crop of product 2 (117.5 g) as a tan solid. The filtrate from the tent-butyl methyl ether trituration was purified by concentrating to dryness (793 g) and passed through a plug of silica eluting with ethyl acetate to give 767 g of crude product 2. It was then recrystallised from ethyl acetate (500 ml) to give a third crop of product 2 (126.5 g) as a tan solid. The total amount of product 2 obtained was 840 g (35% yield).

Example 4

Preparation of Octane-Boosting Fuel Additive d Via Route (ii')

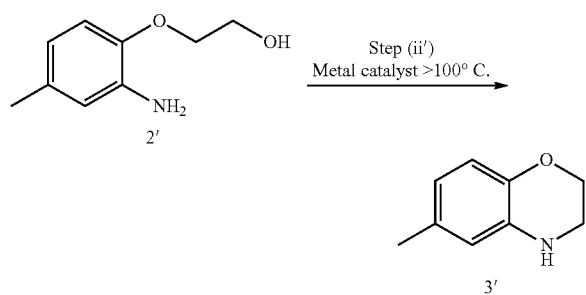

Cyclisation reactions in the presence of a metal catalyst but in the absence of a base, hydrogen or other reaction components were carried out under a variety of conditions. As a general procedure, a mixture of compound 2' and the catalyst were heated, optionally in the presence of a solvent, to the specified temperature. Heating was continued, before cooling to room temperature and sampling for UPLC analysis.

The yields of compound 3' under different conditions are shown in the following table:

| Catalyst | Solvent | Temp (° C.) | Time (hours) | Yield |
|---|---|---|---|---|
| RuCl$_2$(PPh$_3$)$_3$ (1.6 mol %) | none | 145 | 3 | 52% |
| RuCl$_2$(PPh$_3$)$_3$ (2.2 mol %) | NMP | 105 | 3.5 | 3% |
|  |  | 120 | 2 | 5% |
| RuCl$_2$(PPh$_3$)$_3$ (1.7 mol %) | toluene | 105 | 3.5 | 4% |
|  |  | 120 | 2 | 5% |

Further experiments were carried out. As a general procedure, a mixture of compound 2', Raney Ni (50% in water) and mesitylene was heated. The crude reaction mixture was analysed by HPLC to determine conversion and selectivity The yields of compound 3' obtained under different conditions are shown in the following table:

| Solvent volume (eq) | Catalyst amount (eq) | Temp (° C.) | Time (h) | Yield |
|---|---|---|---|---|
| None | 0.6 | 150 | 16.5 | 76% |
|  |  |  | >21 | 84% |
| 16 | 0.2 | 167 | 4 | 11% |
| 1.6 | 0.6 | 150 | 21 | 80% |
| 3.2 | 0.8 | 150 | 21 | 83% |
| 3.2 | 0.6 | 150 | 21 | 88% |
| 1.1 | 0.4 | 140 | 16.5 | 73% |
|  |  |  | 40 | 78% |
| 2.3 | 0.4 | 140 | 16.5 | 59% |
|  |  |  | 40 | 77% |
| 1.1 | 0.2 | 140 | 16.5 | 49% |
|  |  |  | 40 | 70% |
| 2.3 | 0.2 | 140 | 16.5 | 67% |
|  |  |  | 40 | 63% |
| 2.4 | 0.4 | 140 | 67 | 90% |
|  |  |  | 91 | 91% |
| 2.4 | 0.2 | 140 | 67 | 86% |
|  |  |  | 91 | 86% |
| 3.4 | 0.2 | 140 | 67 | 88% |
|  |  |  | 91 | 78% |
| 2.4 | 0.2 | 140 | 67 | 90% |
|  |  |  | 91 | 90% |
| 3.4 | 0.2 | 140 | 67 | 88% |
|  |  |  | 91 | 87% |
| 2.5 | 0.2 | 140 | 69 | 84% |
|  |  |  | 93 | 86% |
| 1.5 | 0.2 | 140 | 69 | 81% |
|  |  |  | 93 | 83% |
| 3.5 | 0.2 | 140 | 69 | 78% |
|  |  |  | 93 | 81% |
| 2.5 | 0.2 | 125 | 69 | 56% |
|  |  |  | 93 | 63% |
| 2.5 | 0.3 | 150 | 5.5 | 80% |
|  |  |  | 21.5 | 91% |
|  |  |  | 26.5 | 91% |
| 2.5 | 0.3 | 150 | 5.5 | 75% |
|  |  |  | 21.5 | 94% |
|  |  |  | 26.5 | 95% |

Further experiments were carried out in the presence of a metal catalyst and hydrogen gas. As a general procedure, catalyst was added to an argon flushed stainless steel autoclave (300 mL). To this was added material 2' (0.33 g, 2.0 mmol) followed by mesitylene (10 mL). The autoclave was sealed, charged to 7 bar with hydrogen and heated to 170° C., except in the cases of Experiments xxxii, xxxiii and xxxiv where the temperature was raised to 210° C. The reaction was held at this temperature for 20 hours, before cooling to room temperature and sampling for UPLC (MeCN) analysis.

The yields of compound 3' obtained under different conditions are shown in the following table:

| Entry | Catalyst (amount) | Yield |
|---|---|---|
| i | Raney Ni (slurry in water) | 53% |
| ii | Ni(65% wp/$Al_2O_3$/$SiO_2$ (10 mol %) | 72% |
| iii | Pd/C (5 wt %) | 5% |
| iv | Pt/C (5 wt %) | 6% |
| v | Ru/C (5 wt %) | 55% |
| vi | Pd/$Al_2O_3$ (5 wt %) | 9% |
| vii | Ru(5% wt)/C (5 wt %) | 80% |
| viii | Pt/C (5 wt %) | 9% |
| ix | Pt/C (5 wt %) | 30% |
| x | Raney Ni (5 wt %) | 75% |
| xi | Raney Ni (5 wt %) | 54% |
| xii | Ni(65% wt/$Al_2O_3$/$SiO_2$ (5 wt %) | 52% |
| xiii | Ni(65 wt %)/$Al_2O_3$/$SiO_2$ (10 mol %) | 72% |
| xiv | Ir(5% wt)/C (5 wt %) | 44% |
| xv | Rh(5% wt)/C (5 wt %) | 11% |
| xvi | Raney Co (5 wt %) | 64% |
| xvii | Pt(5% wt)/$Al_2O_3$ (5 wt %) | 14% |
| xviii | Pt/Fe/C (5 wt %) | 43% |
| xix | Pt/C/Cu(1% wt) (5 wt %) | 51% |
| xx | Raney Cu (5 wt %) | 2% |
| xxi | Rh(5 wt %)/$Al_2O_3$ (5 wt %) | 8% |
| xxii | Pd(5 wt %)/$Al_2O_3$ (5 wt %) | 17% |
| xxiii | Pd(5 wt %)/Lindlars (5 wt %) | 59% |
| xxiv | Pt(5 wt %)/$Al_2O_3$ (5 wt %) | 31% |
| xxv | Pt/C(5 wt %) (5 wt %) | 14% |
| xxvi | Pt(5 wt %)/$SiO_2$ (5 wt %) | 20% |
| xxvii | CuO/ZnO(50 wt %) (5 wt %) | 5% |
| xxviii | CuO(50 wt %)/$Al_2O_3$/MnO (5 wt %) | 12% |
| xxix | Ru(5 wt %)/$Al_2O_3$ (5 wt %) | 26% |
| xxx | Pd/C(5 wt %)/ZnO (5 wt %) | 62% |
| xxxi | Pt/CN(5 wt %) (5 wt %) | 18% |
| xxxii | CuO/ZnO(50 wt %) (5 wt %) | 19% |
| xxxiii | CuO(50 wt %)/$Al_2O_3$/MnO (5 wt %) | 17% |
| xxxiv | $Cu_2Cr_2O_5$ (5 wt %) | 6% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A method for preparing a fuel additive having the formula:

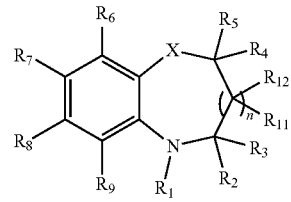

where: $R_1$ is hydrogen;
$R_2$, $R_3$, $R_4$, $R_5$, $R_{11}$ and $R_{12}$ are each independently selected from hydrogen, alkyl, alkoxy, alkoxy-alkyl, secondary amine and tertiary amine groups;
$R_6$, $R_7$, $R_8$ and $R_9$ are each independently selected from hydrogen, alkyl, alkoxy, alkoxy-alkyl, secondary amine and tertiary amine groups;
X is selected from —O— or —$NR_{10}$—, where $R_{10}$ is selected from hydrogen and alkyl groups; and
n is 0 or 1,
provided that at least one of $R_2$, $R_3$, $R_4$, $R_5$, $R_6$, $R_7$, $R_8$, $R_9$, $R_{11}$ and $R_{12}$ is selected from a group other than hydrogen,
said method comprising carrying out the following reaction:

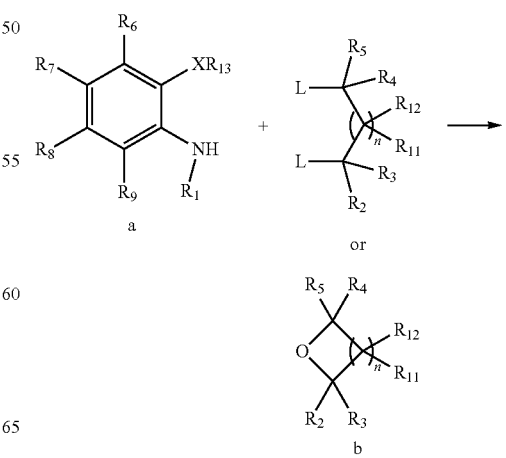

-continued

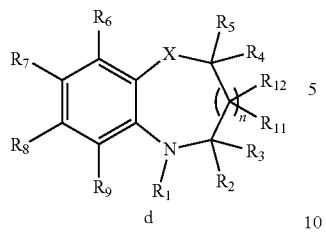

d where: $R_{13}$ is selected from hydrogen and alkyl groups; and
each L is independently selected from leaving groups, or both L groups together form the group —O—C(O)—O—.

2. A method according to claim 1, wherein reagent b is selected from:

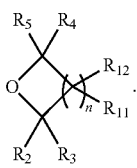

3. A method according to claim 1, wherein reagent b is used in an amount of from 0.5 to 4 molar equivalents as compared to starting material a.

4. A method according to claim 1, wherein the reaction comprises the following sub-steps:

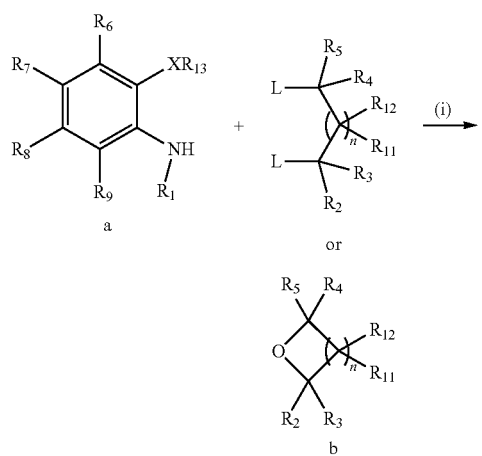

-continued

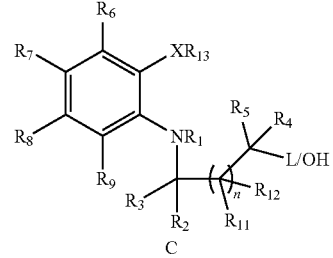

c

↓(ii)

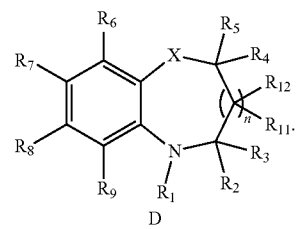

D

5. A method according to claim 4, wherein step (i) is conducted in the presence of a solvent selected from tetrahydrofuran, acetonitrile, dimethoxyethane, dioxane, N-methyl-2-pyrrolidone, dimethylformamide, dimethylacetamide, dimethyl sulfoxide, ethylene carbonate, sulfolane, diphenyl ether, acetonitrile, 2-nitropropane, acetone, butan-2-one, butylformate, ethyl acetate, isobutyronitrile, methylacetate, methyformate, nitromethane, oxolane and propionitrile and water.

6. A method according to claim 4, wherein step (i) is conducted at a temperature of greater than 15° C.

7. A method according to claim 4, wherein step (ii) is conducted in the presence of a hydrogen halide.

8. A method according to claim 7, wherein hydrogen halide is used in an amount of at least 5 molar equivalents as compared to intermediate c.

9. A method according to claim 7, wherein step (ii) is conducted at a temperature of greater than 60° C.

10. A method according to claim 4, wherein the reaction in step (ii) is carried out using a base, where the base is selected from:
    inorganic bases selected from alkali metal hydroxides, alkali metal carbonates and aqueous ammonia; and
    organic bases.

11. A method according to claim 4, wherein step (ii) is conducted in the presence of a trihydrocarbyl phosphone, and an azo compound.

12. A method according to claim 11, wherein step (ii) is conducted in the presence of an aprotic solvent selected from tetrahydrofuran, acetonitrile, dimethoxyethane and dioxane.

13. A method according to claim 1, wherein the reaction comprises the following sub-steps:

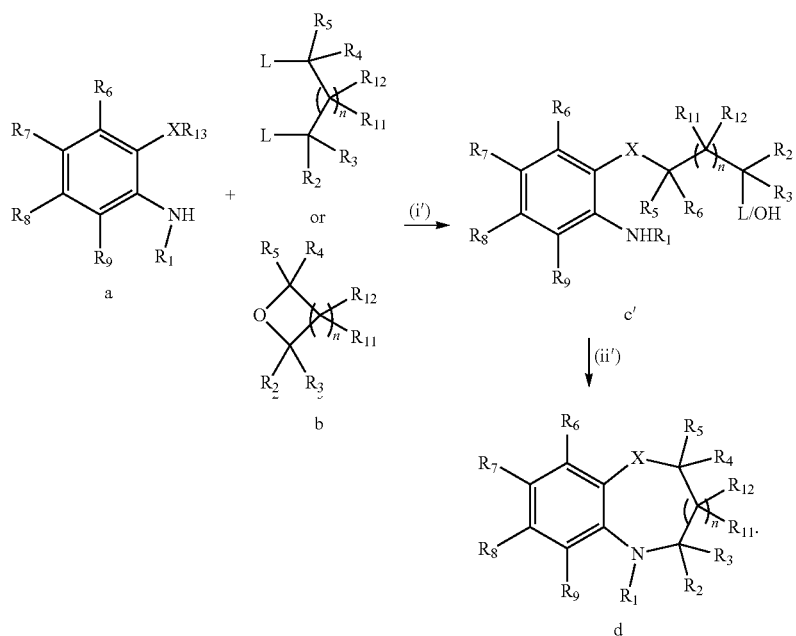

14. A method according to claim 1, wherein $R_{13}$ is selected from hydrogen, methyl, ethyl, propyl and butyl.

15. A method according to claim 1, wherein each L is independently selected from: halides, substituted aryloxy groups, sulfonates and —XH.

16. A method according to claim 1, wherein the method is a batch process in which the fuel additive is produced in a batch quantity of greater than 100 kg.

17. A method according to claim 1, wherein the method is a continuous process.

\* \* \* \* \*